US005801255A

United States Patent [19]

Ohara et al.

[11] Patent Number: 5,801,255
[45] Date of Patent: Sep. 1, 1998

[54] METHOD FOR PRODUCING LACTIDE AND APPARATUS USED THEREFOR

[75] Inventors: Hitomi Ohara, Kyoto; Makoto Ogaito, Nagaokakyo, both of Japan

[73] Assignee: Shimadzu Corporation, Kyoto, Japan

[21] Appl. No.: 690,787

[22] Filed: Aug. 1, 1996

[51] Int. Cl.$^6$ ............................................. C07D 319/12
[52] U.S. Cl. ............................................. 549/274
[58] Field of Search ............................................. 549/274

[56] References Cited

U.S. PATENT DOCUMENTS 5,332,839  7/1994  Benecki et al. ............................ 549/274

*Primary Examiner*—Amelia Owens
*Attorney, Agent, or Firm*—Birch, Stewart, Kolasch & Birch, LLP

[57] ABSTRACT

The method for producing lactide includes the steps of (a) synthesizing lactide using lactic acid as a starting material; (b) discharging in gaseous states lactide synthesized and impurities formed upon synthesis in step (a); (c) liquefying gaseous components in step (b) and solidifying only lactide, to thereby separate the impurities from the thus-obtained solidified lactide; and (d) returning the separated impurities in step (c) back to the synthesis step (a). The apparatus used for the above production includes (a) a reactor for carrying out synthesis of lactide; (b) a means for gasifying synthesized lactide and impurities formed upon synthesis in the reactor (a) and discharging the resulting gaseous components; (c) a means for cooling the gaseous components to liquefy the gaseous components obtained by the means (b) and solidify only lactide; and (d) a pipe for returning to the reactor (a) components which are not solidified by the means (c).

11 Claims, 1 Drawing Sheet

METHOD FOR PRODUCING LACTIDE AND APPARATUS USED THEREFOR

BACKGROUND OF THE INVENTION

1. Field of the Invention

The present invention relates to a method for producing lactide and an apparatus used therefor. More specifically, it relates to a method for producing lactide while carrying out its purification process, and an apparatus used therefor. The lactide produced by the method of the present invention is usable for starting materials for the production of polylactic acids.

2. Discussion of the Related Art

A polylactic acid is a biologically very safe polymer, and its degradated product, namely lactic acid, is absorbed in vivo. Having the above properties, the polylactic acid is useful for medical purposes, including surgical sutures, sustained-release capsules in drug delivery systems, and reinforcing materials for bone fractures. Moreover, it is noted as a biodegradable plastic, because it is degraded under natural environmental conditions. It is also widely used for monoaxially and biaxially stretched films, fibers, extrusion products, and various other purposes.

The methods for producing a polylactic acid include a method wherein a cyclic lactide of lactic acid (dimer), is first synthesized from lactic acid and then purified by such methods as crystallization, followed by ring-opening polymerization. In sum, according to this method, the lactide can be produced by the steps of polymerizing sufficient amounts of lactic acid to give polylactic acids with relatively low molecular weight (oligomers), and then heating the polymerized mixture in the presence of catalysts well known in the field of art, such as antimony trioxide, to give lactide as a component in vaporized products.

However, impurities other than lactide in the vaporized products include water and monomers, dimers, and trimers of lactic acid. Since these impurities act as inhibitors for polymerizing lactide, polylactic acids having high molecular weight cannot be obtained unless high-purity lactide is used. For this reason, it is necessary to purify the impurity-containing lactide, and conventional purification methods for lactide include purification methods employing solvents. For instance, Japanese Patent Laid-Open No. 63-101378 discloses recrystallization using an alcohol having 1 to 6 carbon atoms, preferably isopropyl alcohol, or precipitation from a lactide-insoluble solvent.

In the above conventional purification methods, however, water, lactic acid, and lactic acid oligomers are liable to cause ring-opening of the lactide, thereby resulting in a low yield of the lactide. Also, employing a solvent necessitates equipments for storage and collecting, thereby requiring rather high investment costs in equipment.

In order to solve these problems, proposals have been made for purification methods without employing a solvent (Japanese Patent Laid-Open No. 6-256340). This method is so-called "melt crystallization," wherein repetitive phase conversions from a liquid phase to a solid phase are selectively carried out. In this method, however, since hydroxy impurities, such as oligomers, lactic acid, and water, have to be supplied in a molten state, the lactide is susceptible to ring-opening reaction as in the case where solvents are employed, thereby resulting in a low yield of lactide. Moreover, since the yield is increased by purifying by melt crystallization, the operation of returning oligomers and lactic acid collected as impurities to the reactor further complicates the process, as well as having a large heat loss.

SUMMARY OF THE INVENTION

Therefore, in view of the above problems, an object of the present invention is to provide a novel method for producing lactide without using a solvent while eliminating the problems in the conventional melt crystallization method.

Another object of the present invention is to provide an apparatus used for such a method.

In one aspect, the present invention is concerned with a method for producing lactide, comprising the steps of:

(a) synthesizing lactide using lactic acid as a starting material;

(b) discharging in gaseous state lactide synthesized and impurities formed upon synthesis in step (a);

(c) liquefying gaseous components in step (b) and solidifying only lactide, to thereby separate the impurities from the thus-obtained solidified lactide; and (d) returning the separated impurities in step (c) back to the synthesis step (a).

In another aspect, the present invention is concerned with an apparatus for producing lactide, comprising:

(a) a reactor for carrying out synthesis of lactide;

(b) means for gasifying synthesized lactide and impurities formed upon synthesis in the reactor (a) and discharging the resulting gaseous components;

(c) means for cooling gaseous components to liquefy the gaseous components obtained by the means (b) and solidify only the lactide; and (d) a pipe for returning to the reactor (a) components which are not solidified by means (c).

BRIEF DESCRIPTION OF THE DRAWING

The present invention will become more fully understood from the detailed description given hereinbelow and the accompanying drawing which is given by way of illustration only, and thus, is not limitative of the present invention, and wherein.

Figure 1:
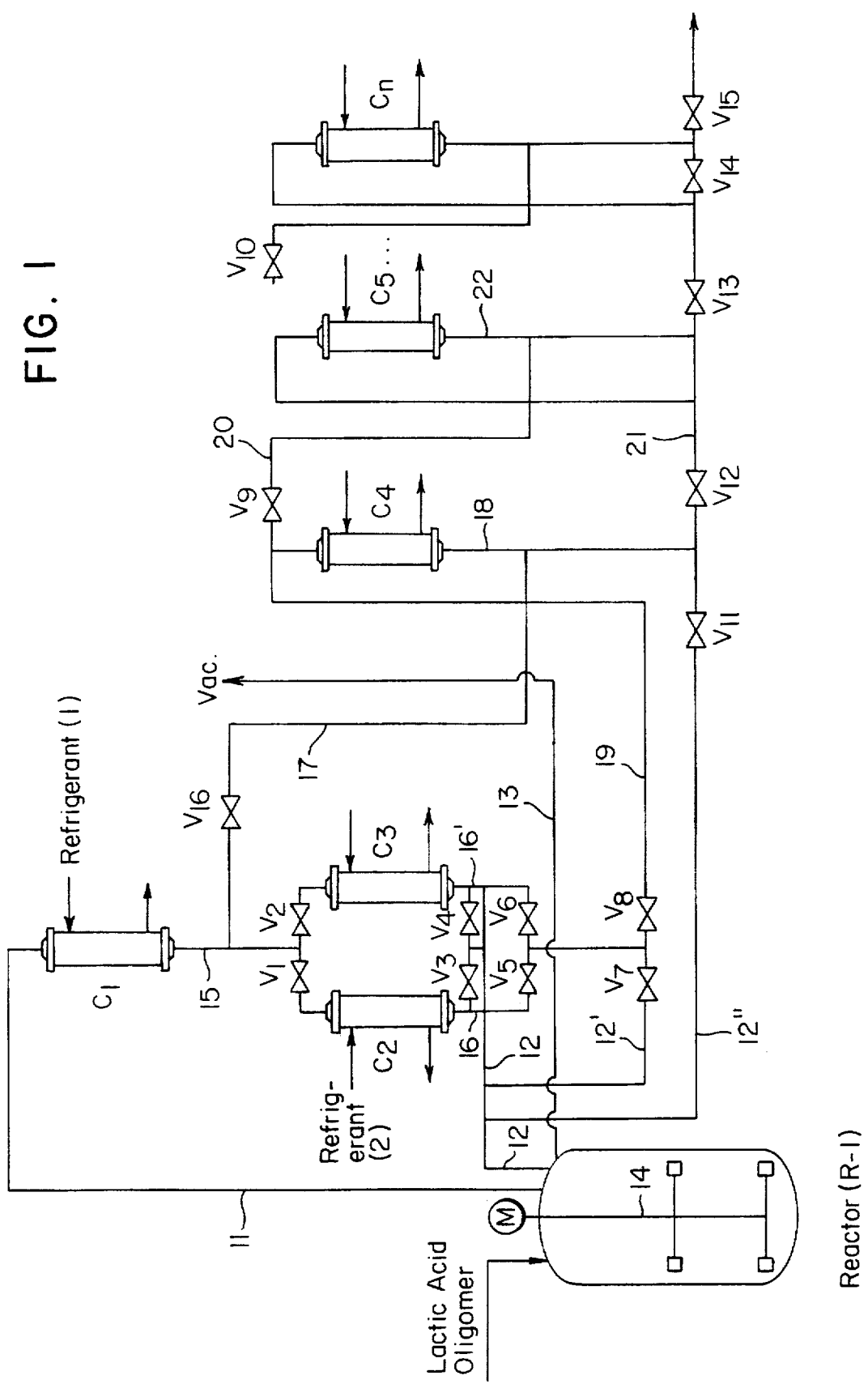
FIG. 1 is a schematic view of an apparatus for carrying out the method of the present invention.

The reference numerals in FIG. 1 denote the following: R-1 is a reactor, 11 a discharge pipe, 12 a returning pipe, 12',12" connecting pipes, 13 a vacuum line, 14 a turbine impeller, 15 a connecting pipe, 16,16' discharge pipes, 17 a connecting pipe, 18 a discharge pipe, 19 a feeding pipe, 20 a connecting pipe, 21 a feeding pipe, 22 a discharge pipe, $C_1$–$C_n$ heat exchangers, and $V_1$–$V_{16}$ valves (on-off switches only).

DETAILED DESCRIPTION OF THE PREFERRED EMBODIMENTS

In the present invention, the lactic acid used as starting materials may be either one of L-lactic acid or D-lactic acid. The lactic acid mentioned above may be any ones produced by the conventionally known methods, with a preference given to ones produced by fermentation method with a purity of 80% or more and an optical purity of 99% or more. The lactic acid mentioned above is dehydrated and concentrated to produce a lactic acid oligomer as an intermediate. The dehydration is carried out generally under a reduced pressure of from 10 to 100 Torr and a temperature of from 130° to 170° C. The resulting lactic acid oligomers have a weight-average molecular weight of preferably from about 400 to about 2,000, more preferably from about 1,000 to about 2,000. The resulting lactic acid oligomers are then formed into cyclic dimers. In other words, the catalysts for forming cyclic dimers (transesterification reaction) are added, and the resulting mixture is heated under a reduced pressure to distill off the lactide. Here, the usable catalysts may be any of conventionally known ones, including tin octylate, antimony trioxide, zinc oxide, and lead stearate. The heat treatment for gasification is carried out under the conditions of a temperature of preferably from 190° to 210° C., and more preferably a reduced pressure of from 10 to 50 Torr.

The reactors usable in the synthesis of the above lactide may be vertical reactors or horizontal reactors. In the cases where the vertical reactors are used, the reactors may be equipped with agitation impellers, including a paddle impeller, a turbine impeller, an anchor impeller, a double-motion impeller, and a spiral ribbon impeller. Among them, a preference is given to a reactor with a spiral ribbon impeller used for stirring in cases where the viscosity is high. In addition, in the cases where the horizontal reactors are used, they may be equipped with agitation impellers, such as single-screw extruders and twin-screw extruders.

The synthesized lactide and impurities formed upon synthesis, such as water, monomers of lactic acid, lactic acid oligomers, have vapor pressures of from 6 to 20 mmHg, so that the lactide and impurities components can be discharged from the reactor by gasifying the components under the production conditions of the lactide given above. Here, the reactor may also function as a gasifying means for gasifying the lactide and impurity components and discharging these gaseous components. Heating to the above-mentioned temperature can be achieved by a known heating means, such as a heater, and a reduced pressure is provided by a vacuum pump.

The gaseous lactide and impurities are then cooled to a temperature equal to or lower than the melting point of the lactide, for instance from 80° to 95° C., and thereby only the lactide is solidified after liquefying the gaseous components. This cooling may be carried out by, for instance, passing a refrigerant through a heat exchanger, without being limited thereto. Here, as for the known refrigerants, such as ethylene glycol, or cooling water or warm water may be employed. The number of the cooling means is not particularly limited, and for example, a plurality of the cooling means having different temperature settings may be provided serially, where the lactide and impurities are passed sequentially.

Also, the temperature of one cooling means does not have to be fixed at a given temperature, and it is preferred that the impurities adhered to the surfaces of the solidified lactide are allowed to leak out by raising the temperature gradually so as not to allow the melting of the solidified lactide. This leak out of the impurities is so-called "sweating," and by the sweating, the small amount of oligomers adhered mainly to the surfaces of the lactide can be removed. The temperature control for allowing sweating to take place may be achieved, for instance, by providing a heater in a cooling means and thus making the electric current flow variable. Alternatively, in the case where cooling water is used for cooling, the temperature control may be achieved by varying temperature of the cooling water. Here, the temperature control is not limited to these methods.

The separation of the lactide and the impurities may be carried out without using a specialized separating means, because the lactide is solidified and the impurities are liquefied to provide a solid-liquid phase in the cooling means. For example, the separation takes place by gravitational action by arranging the cooling means in a gravitational direction. The lactide solidified in the cooling means can be taken out by heating and melting the lactide, and the lactide which is taken out may be re-solidified in the cooling means. Here, the heating and melting of the lactide are carried out at a temperature range not largely exceeding its melting point from the viewpoint of inhibiting degradation of the resulting product.

The separated impurities may be returned to the reactor, for instance, by arranging the reactor underneath the cooling means and returning the impurities by gravitational action, without being limited thereto. Alternatively, the impurities may be returned to the reactor using a liquid-conveying pump. Since the impurities mainly comprise lactic acid oligomers, they may be used for starting materials for forming lactide again.

According to the present invention, of the gaseous lactide and impurities discharged from the reactor, only the lactide is solidified, and the impurities are returned to the reactor to be used again for starting materials for polymerization of the lactide, so that the yield is remarkably improved.

In addition, since the lactide and the impurities are not supplied in a molten state as in the case of melt crystallization, the ring-open reaction of the lactide does not takes place.

A preferred embodiment of an apparatus of the present invention will be described in detail referring to the drawing.

FIG. 1 is a schematic view of an apparatus for carrying out the method of the present invention. In the figure, R-1 is a hollow, cylindrical reactor comprising two openings at its upper portion, an inlet for feeding starting materials for the production of lactide, such as lactic acid oligomers and catalysts, and an exhaust outlet therefor. A discharge pipe 11 is connected to the opening for the exhaust outlet. Also, a turbine impeller 14 is installed inside the reactor R-1, whose motor M is arranged at the side of the other opening (inlet) of the reactor R-1. Further, there are a connection opening connected to the reactor R-1 with a vacuum line 13 for giving a reduced pressure inside the reactor R-1, and a connection opening connected to a returning pipe 12 detailed below. In the periphery of the reactor R-1, a heating means (heater) for heating the reactor R-1 is arranged (not illustrated in the figure), and the temperature inside the reactor R-1 is monitored by a temperature sensor (not illustrated in the figure).

$C_1$, $C_2$, $C_3$, $C_4$, $C_5$, . . . . , $C_n$ are heat exchangers each having a double-cylindrical structure, comprising an inner cylinder through which the produced lactide, etc. flow, and an outer cylinder through which refrigerants such as ethylene glycol flow. Therefore, a heat exchange is conducted between the inner cylinder and the outer cylinder, so that the heat exchanger acts as a cooling means. In addition, in these heat exchangers $C_1$ to $C_n$, the temperature of the refrigerant is raised in the case where the solidified product, namely lactide, is to be melted. Incidentally, the inlets of the heat exchangers $C_1$ to $C_n$ may be located on either a top or bottom portion thereof, with a preference given to a case where the inlet is arranged at the top portion, and the outlet at the bottom portion (In all cases of this embodiment of the present invention, the inlet side is at the top portion of the figure, and the outlet side is at the bottom portion of the figure.).

The above-described discharge pipe 11 is connected to the inlet side of the heat exchanger $C_1$, and a connecting pipe 15 communicating with a pair of heat exchangers $C_2$ and $C_3$ is connected to the outlet side of the heat exchanger $C_1$. The connecting pipe 15 is communicated with a connecting pipe 17, and the connecting pipe 17 is connected to a discharge pipe 18 of a heat exchanger $C_4$, thereby making it possible to feed the obtained product back from the heat exchanger $C_4$ to the pair of heat exchangers $C_2$ and $C_3$. Also, a pair of discharge pipes 16, 16', arranged at the outlets of the pair of the heat exchangers $C_2$ and $C_3$ are connected to the returning pipe 12 to the reactor R-1 at halfway, and a merging point of the discharge pipes 16, 16' is communicated with a feeding pipe 19, the feeding pipe 19 being communicated with the heat exchanger $C_4$. Incidentally, the feeding pipe 19 is connected to the returning pipe 12 via a connecting pipe 12'. Similarly, the above-described discharge pipe 18 of the heat exchanger. $C_4$ is connected to the returning pipe 12 via a connecting pipe 12".

In addition, 20 is a connecting pipe for returning obtained products from a heat exchanger $C_5$ to the heat exchanger $C_4$, the connecting pipe 20 being communicated with a discharge pipe 22 arranged at an outlet side of a heat exchanger $C_5$. 21 is a feeding pipe connected to the discharge pipe 18 of the heat exchanger $C_4$, which is also connected to the inlet side of the heat exchanger $C_5$.

Similar connections are arranged for heat exchangers from $C_5$ to $C_n$ as described above.

Incidentally, $V_1$ to $V_{16}$ are valves (on-off switches only).

Using the above construction, the lactide in the present invention is produced by the following method.

First, lactic acid or oligomers used as starting materials are placed in a reactor R-1. After adding a catalyst, the reactor is subjected to a reduced pressure using a vacuum line 13, while heating with a heating means not illustrated in the figure to synthesize lactide. A mixture of the produced lactide and impurities including oligomers are in gaseous forms, and the above mixture is collectively hereinafter referred to as "crude lactide." The gaseous crude lactide flows through a discharge pipe 11 to be fed into a heat exchanger $C_1$.

In the heat exchanger $C_1$ where a refrigerant kept at a temperature for liquefying the crude lactide flows therethrough, the crude, solid lactide is liquefied. Here, only a valve $V_1$ is open, and the remaining valves $V_2$, $V_3$, $V_4$, ..., $V_{16}$ are closed. The liquefied crude lactide is fed into a heat exchanger $C_2$ through the valve $V_1$. In the heat exchanger $C_2$ where the heat exchanger is previously cooled to a temperature of about the melting point of the lactide by a refrigerant, only the liquefied crude lactide fed thereto is solidified, whereas the impurity components, such as oligomers, remain in liquid states without undergoing solidification. Therefore, the impurities are returned to the reactor R-1 via the returning pipe 12 by opening the valve $V_3$. Thereafter, the temperature inside the heat exchanger $C_2$ is raised to a temperature slightly lower than the melting point of the lactide, for instance, raised to a temperature lower than the melting point of the lactide by about 2 to about 3° C., by a heating means not shown in the figure, to conduct "sweating." The sweated components are then removed from the solidified lactide. In a preferred embodiment, the sweated components are returned in the same manner as above to the reactor R-1. As the sweating begins, the valve $V_1$ is closed and the valve $V_2$ is opened, so that the fluidal product from the heat exchanger $C_1$ is fed into the heat exchanger $C_3$.

After the sweated components are removed, the temperature of the heat exchanger $C_2$ is raised to a temperature where the L-lactide is melted, at which point a valve $V_3$ is closed and valves $V_5$ and $V_8$ are opened to feed the molten lactide to the heat exchanger $C_4$ via a discharge pipe 16 and a feeding pipe 19. The heat exchanger $C_4$ is previously cooled, to solidify again the liquid fed thereinto. In the heat exchanger $C_4$, the procedures of sweating and dissolution are again carried out. In the case where large amounts of the lactide are contained in the sweated components, the sweated components are returned again to the heat exchanger $C_2$ (or the heat exchanger $C_3$) by opening a valve $V_{16}$ and allowing them to pass through the discharge pipe 18 and the connecting pipe 17, and in the heat exchanger, the procedures of solidification, sweating, and dissolution are carried out. The above procedures are repeated until a desired level of purity of 99.9% or higher (or optical purity of 99.9% or higher for those obtainable by using lactic acids with optical activity) is achieved. The sweated components are returned to at least a step before the step where sweating is carried out, for instance, $C_2 \rightarrow$R-1 and $C_5 \rightarrow C_4$, depending upon the lactide content in the sweated components. In other words, in the case where sweating is carried out at a heat exchanger $C_n$, the sweated components are conveyed to the reactor R-1 when the amount of the lactide is small, and the sweated components are conveyed to a heat exchanger $C_{n-1}$, wherein the components are subjected to solidification and sweating to remove the impurities, and then the solidified lactide is heated and dissolved to convey the purified components to the heat exchanger $C_n$.

Incidentally, the melting point of L- or D-lactide is 98° C., whereas the melting point of DL-lactide is 127° C. Therefore, when sweating is carried out, the L- or D-lactide dissolves before the DL-lactide dissolves.

After the L-lactide is dissolved, the temperature may be further raised to dissolve the DL-lactide, and these lactide components may be returned to the reactor R-1 or fed into a separate tank (not illustrated in the figure). If the component is returned to the reactor R-1, the racemization of D-isomers with L-isomers also takes place, thereby causing an increase in the yield of the L-isomers. In addition, the heat exchanger $C_1$ is not necessarily required.

According to the method of the present invention, since the lactide and the impurities are discharged from the reactor in gaseous states, the ring-opening reaction of the lactide during synthesis is not likely to take place as in the case of melt crystallization. Moreover, since the starting materials for lactide synthesis, such as lactic acid oligomers, are returned to the reactor, the resulting lactide can be obtained at a remarkably high yield.

EXAMPLES

The method of the present invention is described in more detail below, without intending to limit the scope of the present invention thereto.

The molecular weight determined by GPC and the optical purity determined by HPLC in the following Experimental Example were analyzed under the following conditions:

<Measurement of Molecular Weight: GPC Measurement>

Detector: RID-6A
Pump: LC-9A
Column oven: CTO-6A
Columns: Connecting in series: SHIM PACK GPC-801C, GPC-804C, GPC-806C, and GPC-8025C.

Here, the detector, the pump, the column oven, and the columns were all manufactured by Shimadzu Corporation.

Analysis conditions:
Solvent: Chloroform
Flow rate: 1 ml/min
Amount of sample: 200 µl (dissolving concentration of 0.5% by weight in chloroform)

Column temp.: 40° C.
<Measurement of Optical Purity: HPLC Measurement>
Pump: LC-6A
Column: CRS10W (manufactured by Mitsubishi Chemical Corporation
Detector: Spectrophotometer (SPD-6AV)
Column temp.: 30° C.
Flow rate: 0.5 ml/min
Eluent: 2 mM Copper sulfate solution Experimental Example Using the apparatus described above, the following experiment was conducted.

1000 kg of a 90% by weight lactic acid solution (the remaining 10% by weight being water), the L-lactide:D-lactide ratio being 99:1, was used as a starting material, and the solution was concentrated and then proceeded with dehydration condensation, to remove 280 kg of water. The resulting oligomer had a weight-average molecular weight determined by GPC of from 1,000 to 2,000. In addition, 25 mg of this oligomer was placed in a test tube to which 2 cc of 1 N-NaOH solution was added. After the test tube was sealed, it was heated at 100° C. for 10 minutes. The reaction mixture was neutralized with 2 cc of 1 N-sulfuric acid solution, and the resulting solution diluted 10 times by volume with distilled water.

When an optical purity of the above sample was determined by an HPLC measurement, the L-lactide content was dropped to 90% by weight owing to heat treatment. Three kilograms of tin octylate were added to the above reaction mixture obtained after removal of water by subjecting to dehydration and condensation, to discharge gasified crude lactide at 200° C. and 15 mmHg. The generated gas was cooled to a gas temperature of 95° C. in a heat exchanger ($C_1$) made of carbide having a heat conduction area of 3 $m^2$, to liquefy the crude lactide. The liquefied lactide and the impurities such as oligomers were conveyed to a heat exchanger ($C_2$) made of carbide having a heat conduction area of 10 $m^2$ with an internal temperature of 93° C., and crystals were formed and adhered to the inner walls of the heat exchanger. Here, the oligomers were not solidified and returned to the reactor R-1.

Thereafter, the temperature inside the heat exchanger $C_2$ was raised to 96° C. to allow sweating to take place. The sweated components were also returned, namely back to the reactor R-1. Further, the temperature inside the heat exchanger $C_2$ was changed to 100° C. to thereby dissolve the crystals. The heated liquid mixture was then conveyed to a heat exchanger $C_4$ with a multi-piped structure having a conduction area of 10 $m^2$. The temperature inside the heat exchanger $C_4$ was previously set at 93° C., and the above operations of sweating and dissolution were repeated. The resulting sweated components were also returned to the reactor R-1.

By carrying out the above operations, the lactide was obtained at a high yield of 95%, which was remarkably higher than a case where the sweated components were not returned, thereby giving a low yield of lactide of 70%. Here, the content of DL-lactide was also remarkably low of 1% or less.

10 g of the resulting lactide was placed in a test tube, and the lactide was polymerized at 140° C. in the presence of 100 ppm of tin octylate. As a result, a polylactic acid polymer having a weight-average molecular weight determined by GPC of 270,000 was obtained.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing lactide, comprising the steps of:
    (a) synthesizing lactide from lactic acid;
    (b) gasifying the synthesized lactide and impurities formed in step (a);
    (c) cooling the gaseous lactide and the gaseous impurities to solidify only the gaseous lactide and to separate the solidified lactide from the impurities;
    (d) raising the temperature of the solidified lactide without melting the solidified lactide and to leak out the impurities from the solidified lactide; and
    (e) returning the impurities in step (c) back to step (a).

2. The method according to claim 1, wherein the synthesized lactide and impurities are heated to a temperature of from 190° to 210° C. to gasify the lactide and impurities in step (b).

3. The method according to claim 1, wherein the synthesized lactide and impurities are gasified in a reactor used for synthesis of lactide in step (a).

4. The method according to claim 1, wherein the gasified lactide and impurities are cooled to 80° to 95° C. to only solidify the gaseous lactide in step (c).

5. The method according to claim 1, wherein the synthesized lactide and impurities are treated at a pressure from 10 to 50 Torr.

6. The method according to claim 1, wherein the impurities comprise lactic acid oligomers.

7. The method according to claim 1, wherein in step (d) the temperature is raised to a temperature lower than the melting point of lactide.

8. The method according to claim 1, wherein in step (d) the temperature is raised to a temperature lower than the melting point of lactide by about 2° to 3° C. in order to conduct sweating.

9. The method according to claim 1, wherein the level of purity of the lactide is 95% or higher.

10. The method according to claim 1, wherein the level of purity of the lactide is 99.9% or higher.

11. The method according to claim 1, further comprising the step of returning impurities in step (d) to step (a).

* * * * *